(12) United States Patent
Iwashita et al.

(10) Patent No.: US 8,147,752 B2
(45) Date of Patent: Apr. 3, 2012

(54) STERILANTS AND STERILIZATION METHOD FOR ASEPTIC FILLING

(75) Inventors: Takeshi Iwashita, Kanagawa (JP); Chikako Sunohara, Kanagawa (JP); Kenichi Kominami, Kanagawa (JP)

(73) Assignee: Toyo Seikan Kaisha, Ltd., Tokyo (JP)

( * ) Notice: Subject to any disclaimer, the term of this patent is extended or adjusted under 35 U.S.C. 154(b) by 366 days.

(21) Appl. No.: 12/304,838

(22) PCT Filed: Jun. 21, 2006

(86) PCT No.: PCT/JP2006/312846
§ 371 (c)(1),
(2), (4) Date: Dec. 15, 2008

(87) PCT Pub. No.: WO2007/148410
PCT Pub. Date: Dec. 27, 2007

(65) Prior Publication Data
US 2009/0311134 A1    Dec. 17, 2009

(51) Int. Cl.
*A61L 2/18* (2006.01)
(52) U.S. Cl. .......................................... 422/28
(58) Field of Classification Search ............... 422/28
See application file for complete search history.

(56) References Cited

U.S. PATENT DOCUMENTS
5,632,676 A * 5/1997 Kurschner et al. ............ 452/173

FOREIGN PATENT DOCUMENTS
| JP | 08058744 A | * | 3/1996 |
| JP | 3080347 B2 | | 8/2000 |
| JP | 2006-069672 A | | 3/2006 |

OTHER PUBLICATIONS

English Translation of Japanese Document No. JP 08058744 provided by the Industrial Property Digital Library: Iwashita, Takeshi; Method and Device for Sterilizing Food Container; May 3, 1996.*
International Search Report of PCT/JP2006/312846, Mailing Date of Sep. 12, 2006.

* cited by examiner

*Primary Examiner* — Kevin Joyner
(74) *Attorney, Agent, or Firm* — Westermina, Hattori, Daniels & Adrian, LLP

(57) ABSTRACT

The present invention provides an aqueous solution of a sterilant of peracetic acid series for use in aseptic filling comprised predominantly of hydrogen peroxide, peracetic acid and water wherein a pH of the aqueous solution is 2~4, a ratio of the concentration of hydrogen peroxide/the concentration of peracetic acid is 0.7 or less, and the concentration of peracetic acid is 500~3000 ppm as well as a sterilization method wherein the sterilant thereof is used. The sterilant of peracetic acid series exhibits an excellent sterilizing effect even at an extremely low concentration of peracetic acid and so is economically advantageous. What is more, washing of the sterilant with sterile water after sterilization of a container is attained by injecting sterile water even for a short period of time to such level that the sterilized container can be filled with foods and drinks, so that the sterilant is remarkable in economical value and working efficiency. The sterilization method is carried out by heating the sterilant of peracetic acid series and/or a container for foods and the like or the interior surface thereof at 60° C. or higher to obtain more effective sterilizing effect and can be used in a recycling system, so far as a ratio of the concentration of hydrogen peroxide/the concentration of peracetic acid be maintained.

3 Claims, 2 Drawing Sheets

STERILANTS AND STERILIZATION METHOD FOR ASEPTIC FILLING

TECHNICAL FIELD

The present invention relates to a sterilant and a sterilization method for keeping plastic or metal containers in combination with closures and covers thereof in a sterility state which are to be filled with various eating and drinking products as well as medical supplies offered for aseptic filling, and keeping various facilities installed in sterility filling space in a sterility state.

BACKGROUND ART

As a method for sterilizing food containers (for example, bottles), known from the past is a method wherein hot water is injected into the interior of the food containers or a method wherein the containers are sterilized with a sterilant of peracetic acid series. The techniques disclosed in patent literatures 1 and 2 proposed by the present inventors are examples of the art thereof.

The patent literature 1 relates to a method wherein food containers are initially brought into contact with hot water above 63° C. to effect sterilization of bacteria of *Penicillium* which are sterilized only with hot water and thereafter spore-forming bacteria capable of forming spores such as bacteria of *Bacillus* as well as fungi having ascospores such as *Neosartorya* which are unable to be sterilized only with hot water are sterilized with a sterilant comprising an aqueous solution of peracetic acid, so as to sterilize food containers effectively without using hot water and the sterilant of peracetic acid series in an amount more than the necessary amount.

The patent literature 2 relates to a method wherein a sterilant of peracetic acid series containing peracetic acid at a concentration of 1000~1500 ppm together with hydrogen peroxide is heated at 60° C. or higher and is injected by the aid of a nozzle into at least the interior of a PET bottle to effect sterilization of the PET bottle.

In sterilization of containers with a sterilant of peracetic acid series, there is either an uneconomical factor in prolonging the sterilizing time for achieving sufficient sterilization or a requisite that the concentration of the sterilant of peracetic acid series is to be decreased for satisfactorily washing the sterilized containers with sterile water after sterilization. Hence, a beneficial way has hitherto been required for conducting sterilization with the sterilant of peracetic acid series having a low concentration within a short period of time. The patent literature 2 is evaluated as a technique capable of solving such problems.

[Patent Literature 1] Japanese Patent No. 3,201,133
[Patent Literature 2] Japanese Patent No. 3,080,347

As a result of continuing extensive research by tracing the aforesaid inventions to develop economical containers and accessories offered for aseptic filling and being capable of exhibiting a sterilizing effect within a short period of time and to develop a sterilization method for the interior of sterilizing apparatus for aseptic filling, it has been discovered surprisingly by the present inventors that a sterilization method exhibiting an extremely high sterilizing effect can be established by mixing hydrogen peroxide with peracetic acid at a concentration lower than the concentration of the peracetic acid and maintaining the concentration of peracetic acid at 500-3000 ppm, nevertheless it is a common sense in a sterilant of peracetic acid series comprising peracetic acid incorporated with hydrogen peroxide that the proportion of hydrogen peroxide is hitherto greater, i.e. a ratio of hydrogen peroxide/peracetic acid being at least 1. The present invention has been accomplished on the basis of the above finding.

DISCLOSURE OF THE INVENTION

The present invention is concerned with an aqueous solution of sterilant of peracetic acid series capable of exhibiting a strong sterilizing (bactericidal) effect with the use of a very small amount of the sterilizing ingredient and having a ratio of the concentration of hydrogen peroxide/the concentration of peracetic acid being not more than 0.7 and the concentration of peracetic acid being 500-3000 ppm as well as a sterilization method thereof, and is featured by displaying a strong sterilizing effect on spores of *Bacillus cereus* which is regarded as a microorganism causing food poisoning and obtaining a sterilant of peracetic acid series in stable state by defining pH at 2~4, which sterilant is more economical as compared with a conventional sterilant of peracetic acid series in the reduced use of hydrogen peroxide and having such a merit that washing of the sterilant after use is easily carried out with a small amount of sterile water within a short period of time.

<Method of Measuring the Concentrations of Hydrogen Peroxide and Peracetic Acid>

The concentration of hydrogen peroxide and the concentration of peracetic acid in the present invention are measured by way of the potassium permanganate-iodine method.

More precisely, a test sample is measured for the concentration of hydrogen peroxide by the potassium permanganate titration under an acidic condition with sulfuric acid and then by adding potassium iodide and a starch indicator to the sample followed by the potassium thiosulfate titration for measuring the concentration of peracetic acid.

By the term "sterilant" used in the present invention is meant a substance aiming at sterilizing (bactericidal) effect in a broad concept including sterilizing or sterile effect. Above all, the sterilant of the present invention contemplates one having a sterilizing effect index of at least 4D.

In evaluation of the sterilizing effect, the evaluation value according to the suspension method generally known as suspension test is said to be generally higher in accuracy. In the present invention, however, evaluation of sterilizing effect was evaluated not only by the suspension test but also by the bottle surface tests and "the method that sterilize bacteria on dry strip by sterilant" known as other evaluation methods and described in Examples.

Defined below is the gist of the present invention.

In accordance with the present invention, there is provided an aqueous solution of a sterilant of peracetic acid series for use in aseptic filling comprised predominantly of hydrogen peroxide, peracetic acid and water wherein a pH of the aqueous solution is 2~4, a ratio of the concentration of hydrogen peroxide/the concentration of peracetic acid is 0.7 or less, and the concentration of peracetic acid is 500~3000 ppm.

In accordance with the present invention, there is also provided an aqueous solution of the aforesaid sterilant of peracetic acid series for use in aseptic filling having a sterile object aimed at being at least one selected from the group consisting of containers for eating and drinking products, containers for medical supplies, closures and covers for the containers, and interior wall of a sterilizing apparatus.

In accordance with the present invention, there is further provided a sterilization method for food containers, which comprised injecting an aqueous solution of the sterilant of peracetic acid series to at least the interior wall of the food containers and washing out the aqueous solution of the sterilant with sterile water.

In accordance with the present invention, there is still further provided the sterilization method wherein the temperature on the surface of the aseptic filling system and/or the aqueous solution of the sterilant of peracetic acid series is maintained at 60~95° C.

In accordance with the present invention, there is still further provided the sterilization method wherein an aqueous solution of the sterilant of peracetic acid series heated at 60~95° C. and in the mixed state with air is injected at least to the interior wall of the aseptic filling system.

BEST MODE FOR CARRYING OUT THE INVENTION

Figure 1:
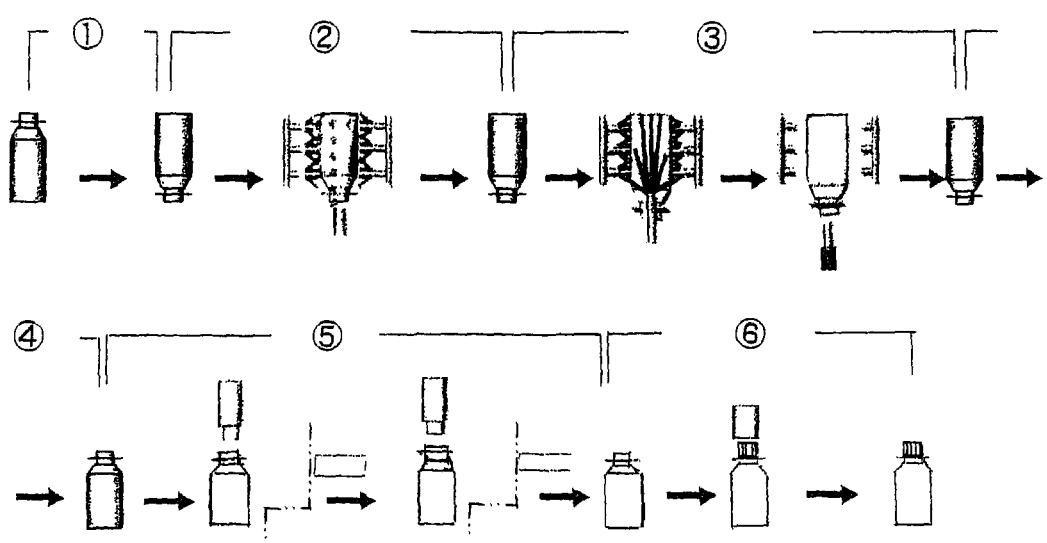
FIG. 1 is a series of process drawings showing a preferable example including the jet sterilization method for carrying out the sterilization method of the present invention.

The present invention is concerned with an aqueous solution of the sterilant of peracetic acid series (it may be referred to hereinafter simply as "the sterilant of peracetic acid series") comprised predominantly of peracetic acid, hydrogen peroxide and water as well as a sterilization method using the aqueous solution. The present invention is characterized by employing the sterilant of peracetic acid series for aseptic filling wherein the pH of the sterilant of peracetic acid series is 2~4, a ratio of the concentration of hydrogen peroxide/the concentration of peracetic acid is 0.7 or less and the concentration of peracetic acid is 500~3000 ppm.

The reason why the pH of the sterilant of peracetic acid series has to be defined as 2~4 is that stability of the sterilant of peracetic acid series is excellent within this range. Above all, stability of the sterilant is especially excellent within the range of 2.5~3.5.

The sterilant of peracetic acid series having a ratio of the concentration of hydrogen peroxide/the concentration of peracetic acid is 1 or less was quite unknown before filing of the present invention. What is more, it is never foreseen from the conventional technical knowledge that an aqueous solution of sterilant of peracetic acid series having a ratio of the concentration of hydrogen peroxide/the concentration of peracetic acid being 0.7 or less and the concentration of peracetic acid being 500~3000 ppm exhibits excellent sterilizing effect.

In the present invention, the fact that a ratio of the concentration of hydrogen peroxide/the concentration of peracetic acid is 0.7 or less actually means that the concentration of hydrogen peroxide is lower than the concentration of peracetic acid, so that the sterilizing effect can be expected even in case of peracetic acid alone containing no hydrogen peroxide.

<Process for Preparing the Sterilant of Peracetic Acid>

The sterilant of peracetic acid series of the present invention contains as main ingredient thereof peracetic acid, hydrogen peroxide and water and may contain acetic acid, an acid or alkali as pH adjusting agent, and a stabilizer for peracetic acid such as 1-hydroxyethylidene-1,1-diphosphonic acid.

Utilizable as the acid for the pH-adjusting agent are sulfuric acid and phosphoric acid. Likewise, sodium hydroxide or the like is utilized as the alkali.

An example of the composition of the sterilant of peracetic acid series currently used is as follows: peracetic acid 10%; hydrogen peroxide 15%; acetic acid 25%; a stabilizer 0.1%; and water 49.9%. The sterilant of this composition is finally diluted with water to have a concentration of 500~3000 ppm whereby the sterilant of peracetic acid series of a concentration as defined in the present invention is obtained.

In the sterilant of the present invention, a ratio of the proportion of the hydrogen peroxide and the acetic acid is adjusted to form peracetic acid under an acidic condition, while the sterilant of peracetic acid series is diluted with water to have a given ratio of the concentration of hydrogen peroxide/the concentration of peracetic acid. The sterilant of peracetic acid series can also be obtained by preparing peracetic acid according to a different process and diluting the acid with water to have a given ratio of the concentration of hydrogen peroxide/the concentration of peracetic acid. Alternatively, the sterilant of peracetic acid can also be obtained by diluting purified peracetic acid itself with water.

It is necessary that the sterilant of peracetic acid series has a ratio of the concentration of hydrogen peroxide/the concentration of peracetic acid is 0.7 or less. It has been found however that a preferable concentration ratio somewhat varies according to either or both of the object to which the sterilant applies on aseptic filling and the temperature or time on injection of the sterilant, or according to the concentration itself of the peracetic acid.

According to the inventors' finding, it has been made clear that the sterilizing effect is excellent at a ratio of the concentration of hydrogen peroxide/the concentration of peracetic acid being 0.5 or less in case the concentration of peracetic acid is within the range from 500 ppm to 1000 ppm, but the sterilizing effect is preferable at a ratio of the concentration of hydrogen peroxide/the concentration of peracetic acid being 0.7 or less in case the concentration of peracetic acid is within the range from 1000 ppm to 2000 ppm. It follows that the concentration of peracetic acid is preferably to be adopted within the range from 500 ppm to 3000 ppm, especially from 500 ppm to 2000 ppm and that the most preferable concentration of peracetic acid is to be adopted by properly adjusting the sterilizing temperature and the sterilizing time.

By the term "the sterilizing (bactericidal) effect" in the present invention is meant the state where the bactericidal level of *Bacillus cereus* ATCC9139 regarded to be a bacteria causing food poisoning reaches at least the level 4D.

The sterilization method of the present invention for food containers may be conducted at normal temperature (20° C.). In this case, however, a prolonged sterilizing time is needed until the object for sterilization reaches the level 4D which is a standard for sterilizing effect. It is preferable therefore that the sterilant of peracetic acid series and/or the food containers are brought to the heated state.

There is no special limitation on the heating condition for sterilization, but the temperature is preferably at least 60° C. and the upper limit of the temperature is preferably about 95° C. so far as the peracetic acid remains without causing any decomposition of the sterilant of peracetic acid series, while considering heat-resistance of the food containers used. Thus, the upper limit is such extent that the sterilant of peracetic acid series may exist in the form of liquid and heat-resistance of the food containers is not damaged.

This heating may be either or both of the object of sterilization, i.e. the aseptic filling system (as generally defined below) and the sterilant of peracetic acid series.

<The Object to which the Sterilant Applies in Aseptic Filling>

In the present invention, the object to which the sterilant applies is not only containers for drinking and eating products and medical supplies offered to aseptic filling but also closures, covers and facilities equipped in aseptic filling space (washing machine, filling device and capping machine) including external surface thereof and inner wall surface forming the boundary surface of the aseptic filling space.

Illustrative of the containers are, for example, various plastic bottles made of polyethylene terephthalate (conventionally called PET bottles) and polyolefin as well as metal bottles. Further, closures and covers used as seal are also included in the intended object of the sterilant.

The sterilant of peracetic acid series of the present invention is injected into at least the interior surface of containers of drinking and eating products and medical supplies as well as closures and covers used for sealing the containers offered for aseptic filling system for attaining sterilization. Referring to FIG. 1 showing a process drawing for jet sterilization, a preferable example is given for the steps for sterilization of aseptic filling system.

FIG. 1 is a schematic drawing showing a series of steps: the container carrying-in zone ①→the container sterilizing zone ②→the container washing zone ③→the container inversion zone ④→the filling zone ⑤→the capping (closing) zone ⑥.

Prior to sterilization of the containers, it is necessary that all the sterilization zones have to be made sterile state by jetting the sterilant of peracetic acid series onto the inner wall surface and then washing the surface with sterile water.

In this step, containers are pinched at the neck portion thereof and introduced in normal standing state into a clean box and made in inverted state. The sterilant of peracetic acid series is then injected into the containers from nozzles positioned at least in the lower portion of the containers through the openings thereof. In this case, it is preferable to provide nozzles for the sterilant so as to inject it toward the outer peripheral wall surface whereby the inner and outer surfaces of the containers are sterilized to the level defined by Food Sanitation Law. The injection time of the sterilant is from 3 seconds to 20 seconds and the sterilized containers are successively conveyed in inverted state to the next washing zone where sterile water is injected into the containers from nozzles positioned in the same way as in the case of injecting the sterilant and also toward the outer peripheral wall surface of the containers.

In case of the present invention, the injection time of sterile water is only about 3 seconds and the containers are washed to such a degree that the sterilant is no longer detected by washing for such a short period of time. The fact that the sterilant can be eliminated perfectly by washing with sterile water within such a short period of time is ascribable to the lower concentration of hydrogen peroxide in the sterilant of the present invention. This point is also an important technical gist of the present invention.

In case of a sterilant having a higher concentration of hydrogen peroxide as in the sterilant known heretofore, the washing operation with sterile water with a short period of time as in the present invention permits remaining of hydrogen peroxide so that it becomes necessary to use a larger amount of sterile water for washing for a longer period of time until foods or medial supplies reach the safe level for filling.

The washed containers in inverted state are turned to a normal standing state and conveyed to the filling zone where the containers are filled with liquid contents. The filled containers are then conveyed to the closing zone (capping) where the containers are sealed with closures previously sterilized and sent to a line for shipment.

The clean box where the containers are sterilized and washed is always kept under superatmospheric pressure for preventing any intrusion of microorganisms and foreign matter.

Figure 2:
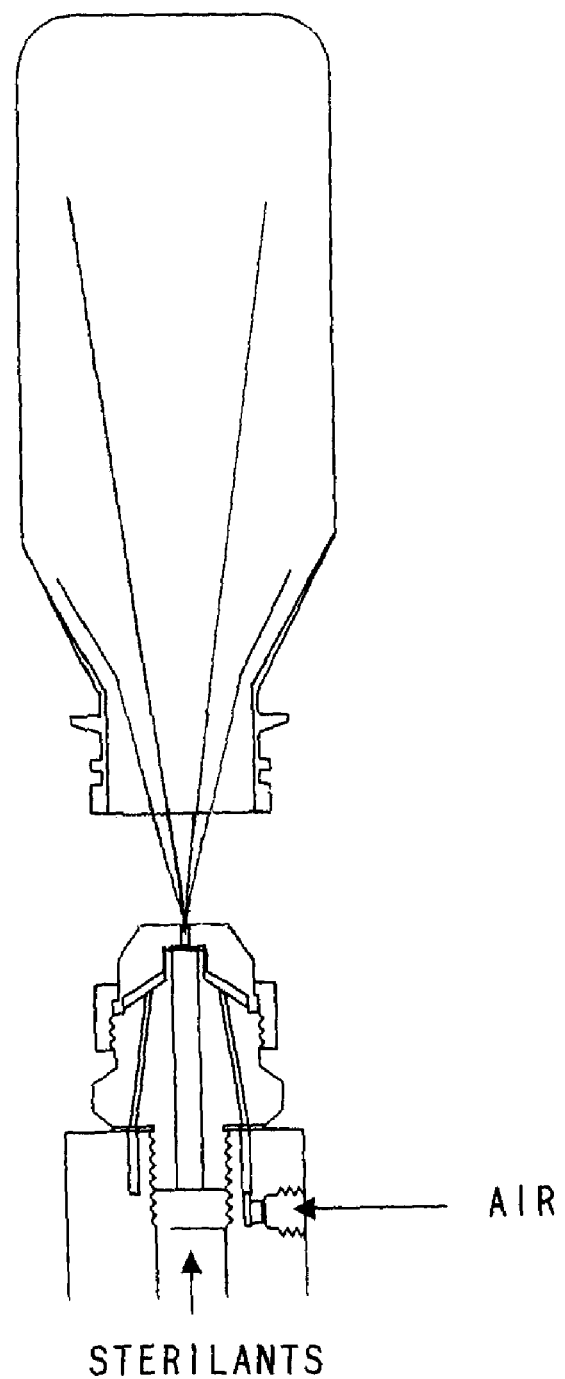
FIG. 2 is a cross sectional view showing a nozzle for injecting an aqueous solution of the sterilant of peracetic acid series in the mixed state with air into a container in the inverted state from the lower opening thereof in the jet sterilization method.

Apart from the foregoing method, another sterilization method for containers comprises pouring the sterilant into the container in normally standing state from the upper position and, after the lapse of a given period of time, the sterilant is evacuated by inverting the container (the so-called "sterilization topping up with the sterilant"). A still another method is "the spraying the sterilant into bottle interior" wherein the sterilant injected from the lower portion of the inverted container is directly hits the bottom of the internal wall of the container and then flows down along the wall of the container, or a method as shown in FIG. 2 wherein the liquid sterilant is jetted in a mixed state with air into the inverted container from the lower portion thereof.

In order to perform the sterilization method for containers accompanied with heating, it is preferable in the present invention to provide a plurality of means for supplying the sterilant of peracetic acid series warmed by temperature-controlling means.

It is possible to recover the injected sterilant and supply it again to a sterilant-supplying system whereby the sterilant can be used in a recycling system.

Concerning the sterilization in the sterilization zone, the sterilant of peracetic acid series is injected into a container or bottle in the state heated to a given temperature, or in other words, on the condition that the sterilizing power of the sterilant is enhanced, so that the time required for sterilization is shortened. Important here is that the sterilant of peracetic acid series has a pH of 2~4, a ratio of the concentration of hydrogen peroxide/the concentration of peracetic acid being 0.7 or less and the concentration of peracetic acid being within the range of 500~3000 ppm.

As is evident from the foregoing descriptions, the sterilant of peracetic acid series has been adjusted to have a pH of 2~4, a ratio of the concentration of hydrogen peroxide/the concentration of peracetic acid being 0.7 or less, and a specifically controlled concentration of peracetic acid and is used for sterilization of the object so that the concentration of the peracetic acid can be decreased to enhance economical value.

EXAMPLES

Example 1

Example 1 shows evaluation of the sterilizing effect in case of varying the sterilizing temperature, the sterilizing effect in case of making the concentration of peracetic acid constant, and the sterilizing effect in case of varying a ratio of the concentration of hydrogen peroxide/the concentration of peracetic acid when the concentration of peracetic acid is 1000 ppm, 2000 ppm and 3000 ppm.

Evaluation of sterilizing effect: Evaluation was made according to the suspension method. A concrete method for the measurement of the evaluation was as follows:

A sample was prepared by adding hydrogen peroxide having a given concentration to the sterilant of peracetic acid series having a prescription of an aqueous solution (prepared from acetic acid 0.3%, sulfuric acid 0.2%, phosphoric acid 0.1%, and sodium hydroxide) containing peracetic acid of a given concentration and having a pH of 2.7~3.3. In Examples 2 and 3 below, a sample was likewise prepared.

To 99 ml of the sterilant of peracetic acid (the measurement temperature, the concentration of peracetic acid and the number of initial living bacteria are as shown in Tables 1 and 2) was added 1 ml of the bacteria suspension so that the concentration of spore suspension might become $10^5 \sim 10^6$.

After the lapse of the function time, a given amount (1 ml) of the solution was added to a solution containing an inactivating agent to inactivate the sterilant ingredient. The number of the residual living bacteria in the liquid containing the inactivating agent was measured according to the membrane filter method using a standard agar medium. The sterilizing or disinfectant effect (D) was obtained from the number of the initial living bacteria and the number of the residual final living bacteria.

Calculation of the sterilizing (disinfectant) effect was carried out according to following equation:

$$D = LOG(N_0/N)$$

wherein $N_0$ stands for the number of the initial living bacteria and $N$ for the number of the residual living bacteria.

An experiment was carried out at n=3, deeming an average number of the residual living bacteria as the number of the residual living bacteria, and a sterilizing effect (D) was evaluated.

A result of the sterilizing (disinfectant) effect evaluated according to the above method is shown in Tables 1 and 2.

Evaluation 1:

In accordance with the conditions shown in Table 1, the disinfectant effect was evaluated by using the sterilant wherein the concentration of peracetic acid (PAA) was made constant (2000 ppm) and the concentration of hydrogen peroxide ($H_2O_2$) was varied from 100 ppm, 1000 ppm and 3000 ppm, and maintaining the sterilizing (disinfectant) time at one minute, 2 minutes, 4 minutes and 8 minutes at 20° C., and the disinfectant time at 8 seconds at 65° C.

As a result of the evaluation, it is observed that the disinfectant effect (above 4D) aimed at was attained at a sterilizing temperature of 20° C. in case of a ratio of the concentration of $H_2O_2$/the concentration of PAA being 0.05 and that in other cases, satisfactory disinfectant effect could not be achieved within the soaking time in the sterilant being 8 minutes Evaluation 2:

In case the sterilizing temperature is maintained at 65° C., it is observed as shown in Table 2 that a satisfactory disinfectant effect was obtained at a ratio of the concentration of $H_2O_2$/the concentration of PAA being 0.7 or less in case of the concentration of PAA being 1000 ppm or 2000 ppm while the disinfectant effect was also satisfactory even at a ratio of the concentration of $H_2O_2$/the concentration of PAA being 0.8 or less in case of the concentration of PAA being 3000 ppm.

TABLE 1

| PAA (ppm) | $H_2O_2$ (ppm) | $H_2O_2$/PAA | Sterilizing time (min.) | | | |
|---|---|---|---|---|---|---|
| | | | 1 | 2 | 3 | 4 |
| 2000 | 100 | 0.05 | 1.3 | 2.7 | 5.8 | 5.8 |
| 2000 | 1300 | 0.65 | 0.4 | 0.8 | 1.4 | 1.7 |
| 2000 | 3000 | 1.50 | 0.1 | 0.2 | 0.5 | 1.1 |

Object of microorganism: *Bacillus cereus* ATCC9139, the number of the initial living bacteria: $3.7 \times 10^5$ cfu/ml.
pH of the sterilant: 2.7~3.3, Temperature of the sterilant: 20° C.,
The numerals in the column of sterilizing time stand for the disinfectant effect (D) on the object of microorganism.

TABLE 2

| PAA (ppm) | $H_2O_2$ (ppm) | $H_2O_2$/PAA | Disinfectant effect (D) |
|---|---|---|---|
| 1000 | 100 | 0.1 | 6.0 |
| | 650 | 0.7 | 4.0 |
| | 1500 | 1.5 | 2.1 |
| 2000 | 200 | 0.1 | >6.0 |
| | 600 | 0.3 | >6.0 |
| | 1400 | 0.7 | 4.8 |
| | 3000 | 1.5 | 2.6 |
| 3000 | 300 | 0.1 | >6.0 |
| | 900 | 0.3 | >6.0 |
| | 2100 | 0.7 | 5.0 |
| | 4500 | 1.5 | 3.8 |

Object of microorganism: *Bacillus cereus* ATCC9139, the number of the initial living bacteria: $5.0 \times 10^5$ cfu/ml.
pH of the sterilant: 2.7~3.3, Temperature of the sterilant: 65° C., Sterilization time: 8 seconds Example 2

Example 2 relates to evaluation of disinfectant effect of the sterilant of peracetic acid series on spores of *Bacillus cereus* according to "the method that sterilizes bacteria on dry strip by the sterilant".

A test piece was a piece of aluminum having a size of 1 cm² carried on the bacteria of $1.5 \times 10^6$, $1.5 \times 10^5$ and $1.5 \times 10^4$ cfu/test piece naturally dried for 24 hours in a clean room (class 1000).

A method of measurement comprised dipping the aforesaid test piece of aluminum into 40 ml of the sterilant of peracetic acid series having a pH of 2.7~3.3 shown in Table 3 for a given period of time. Next, the aluminum test piece was dipped in 5 ml of an inactivating agent which had been sterilized and placed in a test tube. After that, 45 ml of a sterilized SCD liquid culture medium was added to the test tube and existence of any turbidity of the medium was confirmed under a given judging condition to confirm any residual living bacteria. In this case, a sample wherein growth of the bacteria was recognized was recorded as positive, while a sample wherein growth of the bacteria was not recognized was recorded as negative. A number of residual living-bacteria was counted according to the MPN method (n=4) and a disinfectant effect of the sterilant was evaluated from the result of the number of the initial living bacteria and the number of the residual living bacteria.

Judgment condition: An SCD liquid culture medium at 30° C. for one week.

A result is shown in Table 3.

TABLE 3

| PAA (ppm) | $H_2O_2$ (ppm) | $H_2O_2$/PAA | Disinfectant effect (D) |
|---|---|---|---|
| 500 | 50 | 0.1 | 5.0~6.0 |
| | 150 | 0.3 | 4.7~5.0 |
| | 250 | 0.5 | 4.7 |
| | 350 | 0.7 | <4.0 |
| | 400 | 0.8 | <4.0 |
| | 750 | 1.5 | <4.0 |
| 1000 | 100 | 0.1 | >6.0 |
| | 300 | 0.3 | 6.0 |
| | 500 | 0.5 | 5.7 |
| | 700 | 0.7 | 4.7~5.0 |
| | 800 | 0.8 | <4.0 |
| | 1500 | 1.5 | <4.0 |
| 2000 | 200 | 0.1 | >6.0 |
| | 600 | 0.3 | >6.0 |

TABLE 3-continued

| PAA (ppm) | $H_2O_2$ (ppm) | $H_2O_2$/PAA | Disinfectant effect (D) |
|---|---|---|---|
|  | 1000 | 0.5 | >6.0 |
|  | 1400 | 0.7 | >6.0 |
|  | 1600 | 0.8 | 5.0 |
|  | 3000 | 1.5 | 4.5 |
| 3000 | 200 | 0.07 | >6.0 |
|  | 1000 | 0.33 | >6.0 |
|  | 2000 | 0.67 | >6.0 |
|  | 2500 | 0.83 | >6.0 |
|  | 4500 | 1.50 | >6.0 |

Object of microorganism: *Bacillus cereus* ATCC9139, Temperature: 65° C., Time: 8 seconds, the number of the initial living bacteria: $5.0 \times 10^5$ cfu/ml.

Example 3

Example 3 relates to a result of evaluating the disinfectant effect of the sterilant of peracetic acid series of the present invention according to the bottle surface tests.

The sterilization of a bottle made of polyethylene terephthalate of 500 ml in capacity was carried out by using the sterilant of peracetic acid series according to the bottle-inversion jet injection method of the step as shown in FIG. 1 under the following condition:

Sterilant: sterilant of peracetic acid series (pH 2.7~3.3)
Concentration of peracetic acid: 500 pm
Temperature of the sterilant: 55~95° C.
Spray nozzle: Air-assist type internally mixing spray SU12 (FIG. 2 referred to)
Flowing amount of the sterilant: amount of spraying liquid 0.27 liter/min. (0.15 MPa)
Flow rate and temperature of air: amount of air sprayed 15NL/min (0.07 MPa), 30° C.
Opening portion of the bottle and the spray nozzle: not inserted 30 mm
Washing of the bottle after sterilization: The bottle was washed in such manner that the interior surface of the bottle was washed with sterile water by spraying the water into the interior surface of the bottle in inverted state at 1000 ml/second×3 second lest any sterilant should remain in the interior surface of the washed bottle.
The spray nozzle of φ5 was inserted into the bottle by 50 mm from the opening thereof and the sterile water injected from the nozzle was hit the bottom portion of the bottle and exhausted from the opening thereof. The temperature of the sterile water was 30° C.
Manufacture of a sterilized sample bottle: A suspension of the aforesaid test bacteria was prepared at a given concentration and sprayed into the interior surface of a bottle at a given concentration (0.3 ml/bottle) thereby attaching a bacteria suspension onto the interior surface of the bottle.
The bottle was stored in a clean room (class 10000) for 24 hours to dry the interior surface of the bottle.
The manufactured bottle was passed through a sterilizer→washing machine and then tightly sealed with a sterilized closure.
Method of counting the number of the residual living bacteria: A bottle was filled with 500 ml of an SCD liquid culture medium.
The bottle was stored for one week at 30° C. and the culture medium where turbidity was detected was marked as positive while the culture medium where any turbidity was not detected was marked as negative. The number of the residual living bacteria was counted according to the MPN method (n=4) whereby the disinfectant effect was evaluated from the number of the initial living bacteria and the number of the residual living bacteria.
Judging condition: An SCD liquid culture medium 30° C., one week A result of the test is shown in Table 4 wherein ○ stands for a disinfectant effect of 4D or more while x stands for a disinfectant effect of less than 4D.

TABLE 4

| PAA (ppm) | $H_2O_2$ (ppm) | $H_2O_2$/PAA | Temperature of the sterilant (° C.) | | | | |
|---|---|---|---|---|---|---|---|
| | | | 55 | 60 | 65 | 70 | 95 |
| 500 | 50 | 0.10 | X | ○ | ○ | ○ | ○ |
| 500 | 125 | 0.25 | X | ○ | ○ | ○ | ○ |
| 500 | 250 | 0.50 | X | X | ○ | ○ | ○ |
| 500 | 350 | 0.70 | X | X | X | X | ○ |
| 500 | 750 | 1.50 | X | X | X | X | X |

Object of microorganism: *Bacillus cereus* ATCC9139, Sterilizing time: 8 seconds, the number of the initial living bacteria: $5.8 \times 10^5$ cfu/bottle.

What is claimed is:

1. A disinfecting method for a sterile packing system, comprising:
providing a peracetic acid based disinfectant wherein a peracetic acid based disinfectant aqueous solution containing as principal components thereof hydrogen peroxide, peracetic acid, and water has a pH of from 2 to 4, a hydrogen peroxide concentration/peracetic acid concentration ratio of 0.7 or lower, and a peracetic acid concentration of from 500 ppm to 3000 ppm; bringing said disinfectant aqueous solution and/or a disinfectant application inner surface being subjected to sterile packing to a temperature of from 60° C. to 95° C.;
spraying said peracetic acid based disinfectant aqueous solution, in a condition in which air is mixed therewith, onto at least said application inner surface; and subsequently cleaning off said peracetic acid based disinfectant aqueous solution with sterile water.

2. The disinfecting method for a sterile packing system according to claim 1, wherein the application inner surface subjected to sterile packing is at least one surface selected from the group consisting of food and beverage product containers, medical product containers, caps and lids for said containers, equipment installed in sterile packing spaces, and interior wall surfaces forming boundaries for said sterile packing.

3. The disinfecting method of claim 1, wherein the peracetic acid concentration is 3000 ppm.

* * * * *